(12) United States Patent
Dougherty (10) Patent No.: US 11,826,496 B1
(45) Date of Patent: Nov. 28, 2023

(54) DISPERSING SCENT AROUND A VEHICLE

(71) Applicant: Marshall E. Dougherty, Weatherford, OK (US)

(72) Inventor: Marshall E. Dougherty, Weatherford, OK (US)

( * ) Notice: Subject to any disclaimer, the term of this patent is extended or adjusted under 35 U.S.C. 154(b) by 1422 days.

(21) Appl. No.: 16/183,328

(22) Filed: Nov. 7, 2018

Related U.S. Application Data (60) Provisional application No. 62/584,434, filed on Nov. 10, 2017.

(51) Int. Cl.
| | |
|---|---|
| *A61L 9/12* | (2006.01) |
| *F01N 13/08* | (2010.01) |
| *B63J 99/00* | (2009.01) |
| *B60R 19/48* | (2006.01) |
| *F16M 13/02* | (2006.01) |
| *F16B 2/10* | (2006.01) |
| *B60B 1/00* | (2006.01) |

(52) U.S. Cl.
CPC ............ *A61L 9/12* (2013.01); *B60B 1/003* (2013.01); *B60R 19/48* (2013.01); *B63J 99/00* (2013.01); *F01N 13/08* (2013.01); *F16B 2/10* (2013.01); *F16M 13/02* (2013.01); *A61L 2209/15* (2013.01)

(58) Field of Classification Search
CPC ........................................................ A61L 9/12
See application file for complete search history.

(56) References Cited

U.S. PATENT DOCUMENTS

| | | | | |
|---|---|---|---|---|
| 557,676 | A | * | 4/1896 | Heath ............... F16H 27/08 74/435 |
| 3,890,918 | A | * | 6/1975 | Sell ................... B63B 34/67 114/253 |
| 6,065,798 | A | * | 5/2000 | Sankrithi ........... B60P 3/423 296/183.1 |
| 6,080,367 | A | | 6/2000 | Lin |
| 6,398,381 | B1 | * | 6/2002 | Tseng ................. A63H 33/40 362/276 |
| 7,523,605 | B2 | | 4/2009 | Whitaker |
| 8,480,960 | B2 | | 7/2013 | Wheatley et al. |
| D750,767 | S | | 3/2016 | Donovan et al. |

(Continued)

FOREIGN PATENT DOCUMENTS

| | | | |
|---|---|---|---|
| CN | 105561956 A | | 5/2016 |
| DE | 102015001196 | * | 8/2016 |

(Continued)

OTHER PUBLICATIONS

English Machine Translation of DE 102015001196 Belz et al. 2016. (Year: 2016).*

(Continued)

*Primary Examiner* — Donald R Spamer
(74) *Attorney, Agent, or Firm* — Mary M. Lee (57) ABSTRACT

Methods and devices for dispersing scent around the exterior of a vehicle. A scent-dispersing device is attached to the exterior of a vehicle. The device is configured so that the airflow through or around the device causes scent to be dispersed around the vehicle. In one embodiment, the device is installable in the tailpipe of a motorized vehicle so that the exhaust passes through or around the device and thereby disperses scent into the area around the vehicle and into the surrounding environment.

8 Claims, 6 Drawing Sheets

(56) References Cited

U.S. PATENT DOCUMENTS

| | | | |
|---|---|---|---|
| 9,352,064 | B2 | 5/2016 | Furner et al. |
| 9,726,395 | B2 * | 8/2017 | Hammer ............... F24F 13/082 |
| 2009/0004431 | A1 | 1/2009 | Ninomiya |
| 2010/0135866 | A1 | 6/2010 | Mizuno et al. |
| 2010/0254829 | A1 | 10/2010 | Harris |
| 2017/0112955 | A1 | 4/2017 | Bourne |
| 2018/0099065 | A1 | 4/2018 | Burns et al. |

FOREIGN PATENT DOCUMENTS

| | | | |
|---|---|---|---|
| JP | 2000186544 | A | 7/2000 |
| JP | 2009264116 | A | 11/2009 |
| KR | 101375125 | B1 | 3/2014 |
| KR | 20170098390 | A | 8/2017 |

OTHER PUBLICATIONS

Sabertec, LLC, "Blade Tailpipe Exhaust Filter" [online] web page retrieved from http://www.ecooptimized.com, Austin, TX. The first publication date of this reference is unknown. This document was published prior to the effective filing date of the instant application, namely, Nov. 7, 2018, and prior to any foreign priority date of the present application. [retrieved on Nov. 7, 2018].

EHC Teknik LTR, "EHC P15—Particle Filter for starting and moving vehicles indoors" [online] web page retrieved from http://ehcteknik.com/products/ehc-p15/, Partille, Sweden. The first publication date of this reference is unknown. This document was published prior to the effective filing date of the instant application, namely, Nov. 7, 2018, and prior to any foreign priority date of the present application. [retrieved on Oct. 17, 2018].

Induceramic, "Automobile exhaust gas purifying honeycomb ceramics" [online] web page retrieved from http://www.induceramic.com/industrial-ceramics-application/machinery-and-industrial-equipment/air-purification-equipment/automobile-exhaust-gas-purifying-honeycomb-ceramics, Waterloo, Ontario, Canada. The first publication date of this reference is unknown. This document was published prior to the effective filing date of the instant application, namely, Nov. 7, 2018, and prior to any foreign priority date of the present application. [retrieved on Oct. 17, 2018].

Outdoor Supply , Inc., "14 Pack Awning Clamp Set Tarp Clips Snap Hangers Free Ship Survival Emergency" [online] web page retrieved from https://outdoorsupplyinc.com/collections/awning-clamps-straps/products/2-pack-awning-clamp-set-tarp-clips-snap-hangers-free-ship-survival-emergency-new, Isabella CA. The first publication date of this reference is unknown. This document was published prior to the effective filing date of the Instant application, namely, Nov. 7, 2018, and prior to any foreign priority date of the present application. [retrieved on Nov. 7, 2018.

\* cited by examiner

DISPERSING SCENT AROUND A VEHICLE

CROSS-REFERENCE TO RELATED APPLICATION(S)

This application claims the benefit of U.S. provisional application No. 62/584,434 entitled "External Vehicle Scent Device," filed Nov. 10, 2017, the contents of which are incorporated herein by reference.

FIELD OF THE INVENTION

The present invention relates to scent devices generally and, more particularly but without limitation, to devices for dispersing scent external to a vehicle.

BRIEF DESCRIPTION OF THE DRAWINGS

The accompanying drawings, which are incorporated into and form a part of the specification, illustrate one or more embodiments of the present invention and, together with this description, serve to explain the principles of the invention. The drawings merely illustrate a preferred embodiment of the invention and are not to be construed as limiting the scope of the invention.

DETAILED DESCRIPTION OF THE PREFERRED EMBODIMENT(S)

The present invention is directed to devices and methods for dispersing scent around the exterior of a vehicle. There are numerous circumstances where it is useful or desirable to introduce scent into the immediate vicinity of a vehicle. In one application, a scent device may be use to alter the scent of vehicle's exhaust in a hunting environment. For example, it may be desirable to use the scent device of this invention to disperse an attractant when hunting deer or other game.

Alternately, scent emitted from or around a vehicle may pleasantly enhance the overall ambiance of an event. For example, the inventive scent device can be used to impart fragrances in the vicinity of picnics, playgrounds, weddings, birthday parties, and other outdoor activities. Scents evocative of particular holidays may be used at related events. For example, a pine scent may be used at a Christmas party, the fragrance of white lilies may be used on a wedding get-away car, and a pumpkin pie scent may be used at a Thanksgiving celebration. Still further, bubble gum scent may add to the playful atmosphere at a child's birthday party, or food-specific odors may be emitted by a food truck to lure customers.

In accordance with the present invention, a scent device is configured so that air flowing through or around the device entrains scent embedded in the device and disperses it to the surrounding area. Air flow through the device is generated by attaching the device to a vehicle so that some form or air flow created when the vehicle is traveling will cause the device to disperse scent.

In one embodiment, the device is designed for attachment to the tailpipe of a motorized vehicle so that exhaust from the motor generates air flow through the device. In other embodiments, the device may be configured for attachment to other locations on the outside of a vehicle so that, as the vehicle moves, air flow passes through or around the scent device. More specifically, the invention employs the exterior of the vehicle as a mounting location and the vehicle's airflow as a scent dispenser. Thus, the inventive device can effectively mask, reduce, alter, or eliminate odors and/or dispense pleasing fragrances or useful odors into the environment around the vehicle.

As used herein, "vehicle" means any device for carrying a person and includes without limitation, vehicles that are manually driven or self-propelled. As used herein, "vehicle" includes motorized and non-motorized vehicles and includes street and off-road vehicles, including by way of example and without limitation cars, trucks, all-terrain vehicles ("ATV's"), utility task vehicles, side-by-sides, or utility terrain vehicles ("UTV's"), 4-wheelers, motorcycles, golf carts, bicycles, and the like. As used herein, "vehicle" includes vehicles for travel on land or water and, therefore, includes boats.

In accordance with the present invention, the scent device attachable to the exterior of the vehicle so that air flow passing through or over the scent device will disperse the scent. The design of the inventive device will depend where on the vehicle it is to be attached. By way of example only, the scent device may be configured for attachment to a vehicle bumper, a trailer hitch, an antenna, a side rear-view mirror, a wheel or the spoke of a wheel on a bicycle, a front grille, a rollover bar (or roll bar or anti-roll bar or bull bar) on an ATV, a roof rack, or on the tower bar of a speed boat.

To that end, the connector for attaching the scent device to the vehicle may vary widely. As used herein, "connector" refers to any means for attaching the scent device to the vehicle. The connector may be a clip or clamp type mechanism, or a flexible member, such as a strap, tape, or ties. Alternately, the connector may be adhesive or magnetic or operate on suction.

The structure and materials for making the scent device may depend on relevant environmental factors, such as the force of airflow around a moving vehicle, gravity, reaction force on the wheels, drive force by the engine, drag force due to air density and the speed of the vehicle, friction from the road and tires, air resistance on the front of the car. For example, in some embodiments the shape of the device may be aerodynamic, and it may be designed to resist turbulent and irregular air flow. Additionally, the design may accommodate effects of weather, such as heat, cold, and rain. The construction should resist damage from impacts from windbourne debris and hail. In some applications, the device may be sturdy enough to withstand air forces generated by a moving vehicle. For example, the device may need to be heat tolerant, that is, capable of withstanding prolonged exposure to temperatures in excess of 175 degrees Fahrenheit (175° F.).

Figure 1:
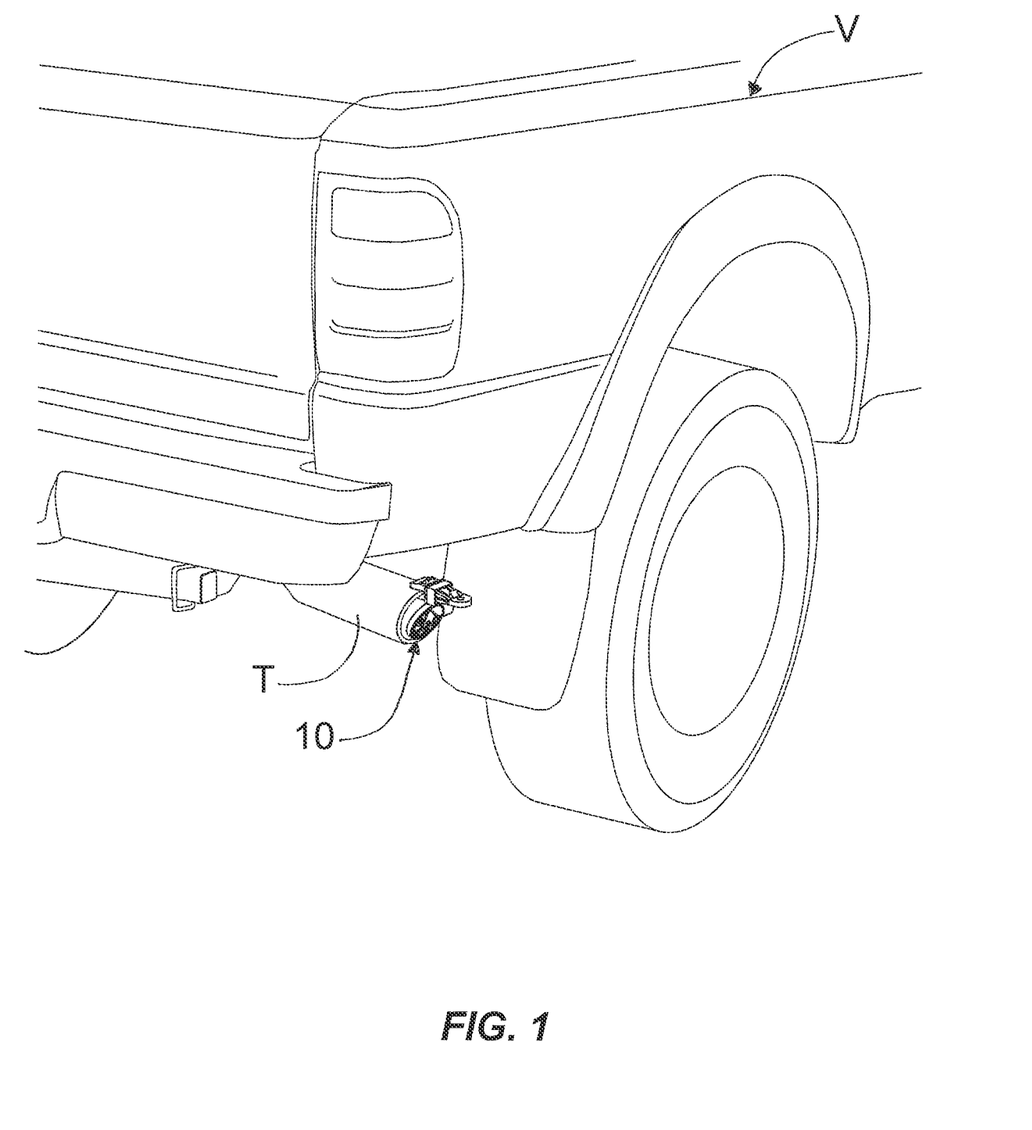
FIG. 1 is a fragmented perspective view of the rear of a pickup truck with the scent device of the present invention installed in the tailpipe so that the engine exhaust will disperse the scent.
Figure 2:
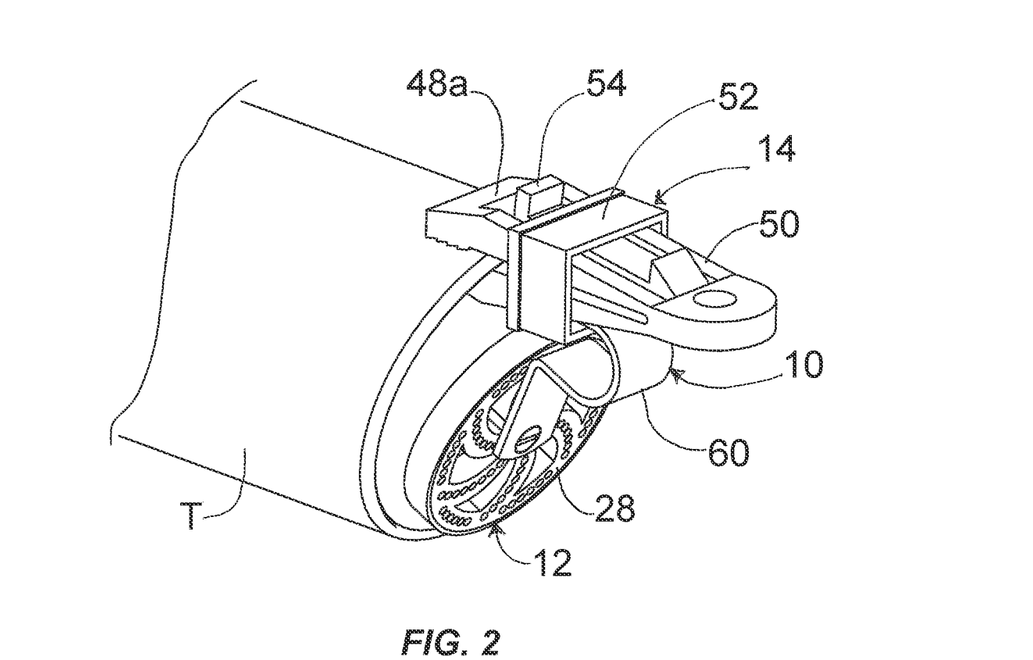
FIG. 2 is an enlarged fragmented perspective view of the tailpipe and attached scent device shown in FIG. 1.
Figure 3:
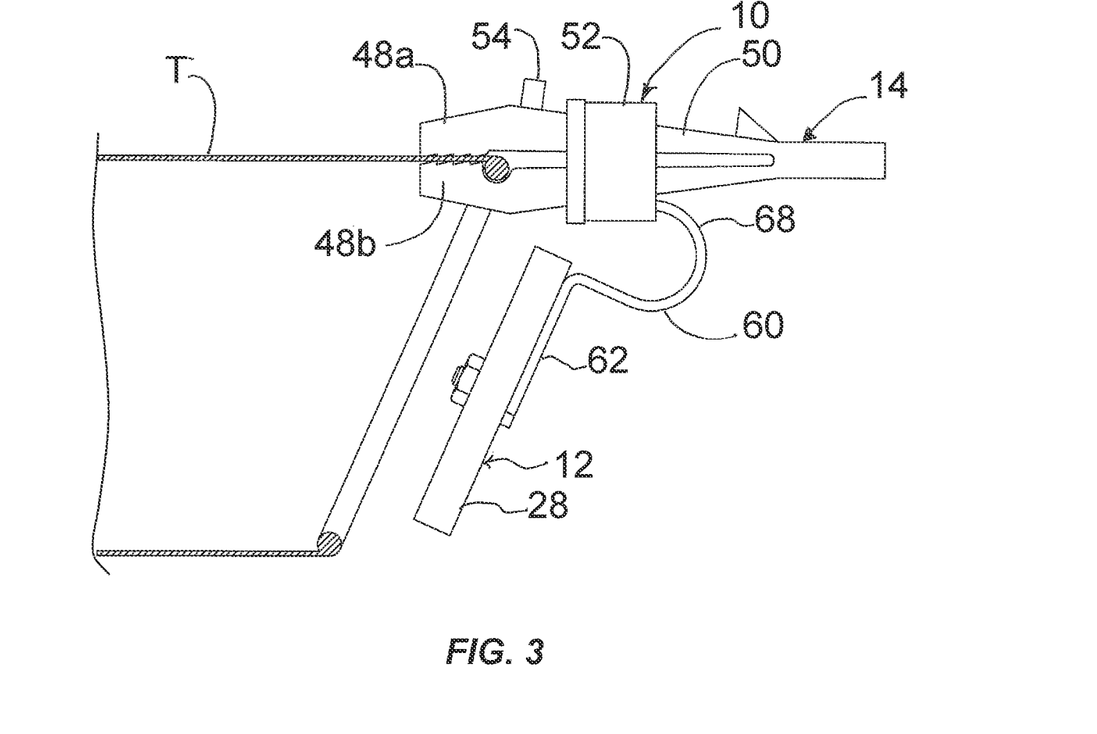
FIG. 3 is a partially sectional side elevational view of the tailpipe and scent device shown in FIG. 2.

Turning now to the drawings in general and to FIGS. 1-3 in particular, there is shown therein a diagram of a motor vehicle "V" equipped with an external scent dispersing device constructed in accordance with one embodiment of the present invention and designated generally by the reference numeral 10. The device 10 is shown mounted in the end of the tailpipe "T" of the vehicle V.

Figure 4:
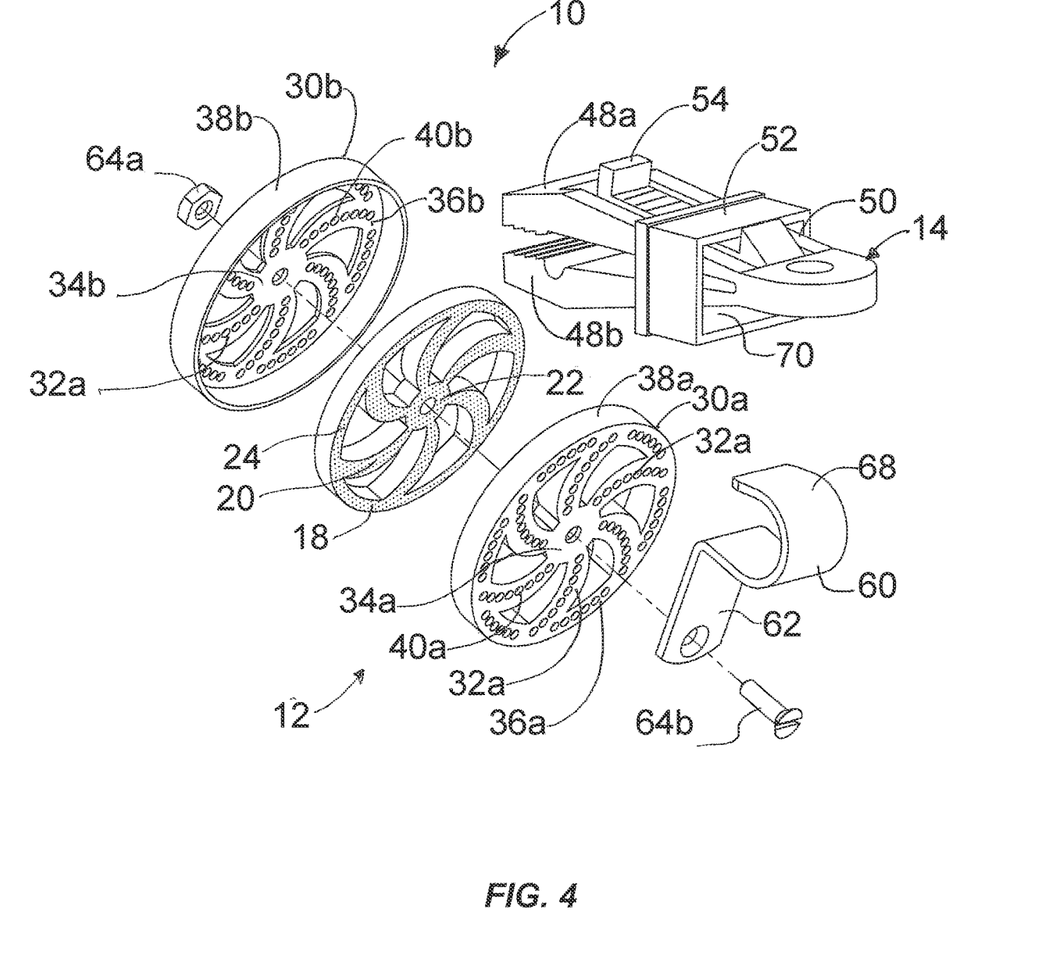
FIG. 4 is an exploded view of the scent device.
Figure 5:
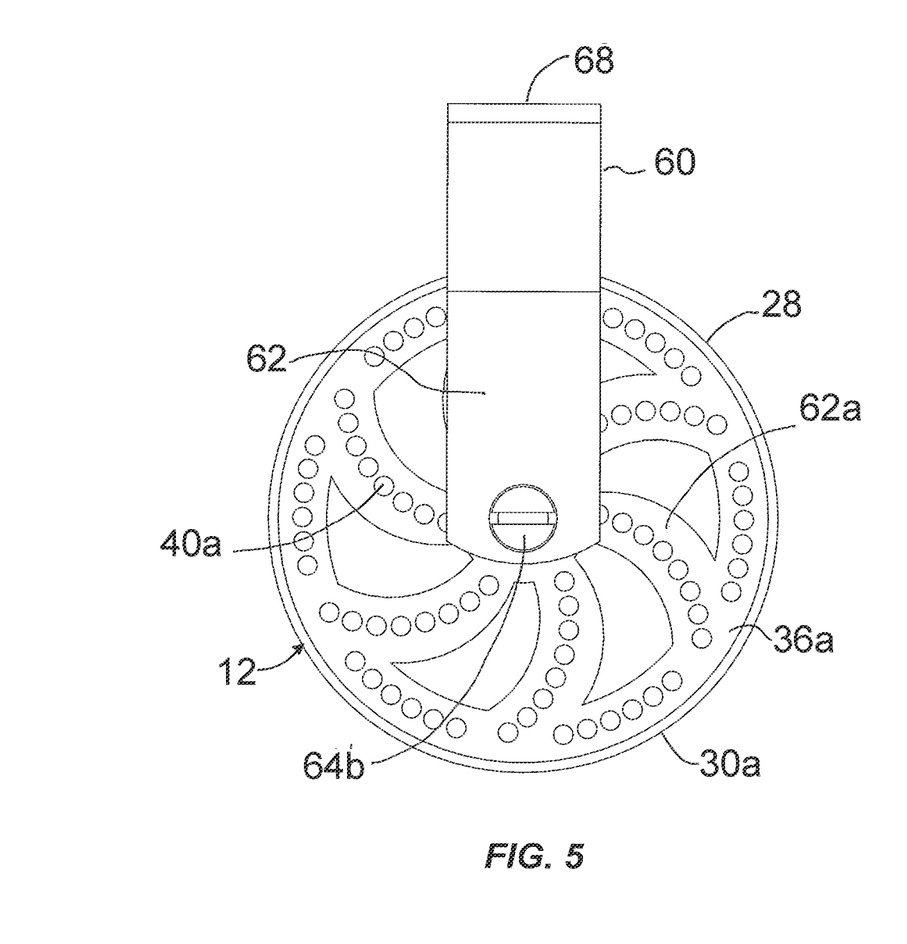
FIG. 5 is a front elevational view of the assembled scent device.
Figure 6:
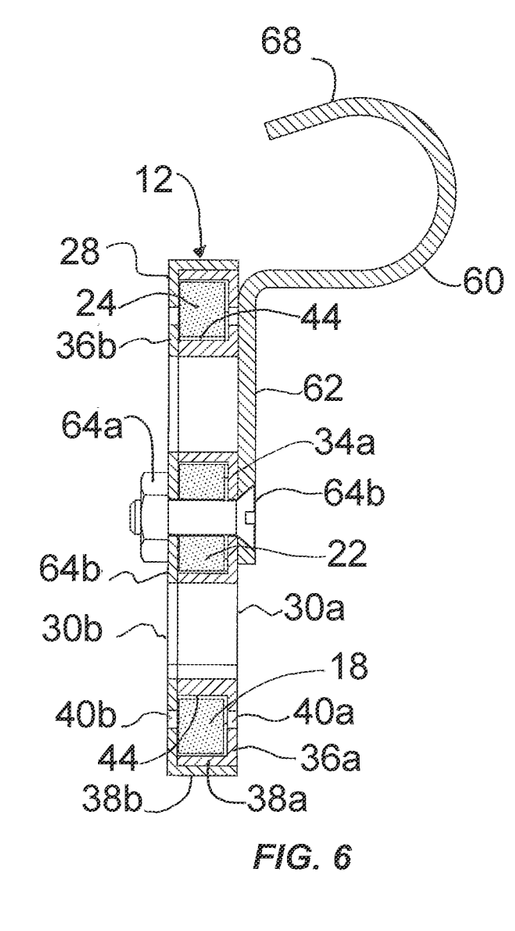
FIG. 6 a side sectional view of the assembled scent device.

With reference now also to FIGS. 4-6, the structure of the device 10 will be explained in more detail. The device 10 generally comprises a frame 12 and a connector 14 for connecting the frame to the tailpipe T. The frame 12 is configured for containing a dispersible scent compound and is sized to fit in the end of the tailpipe T so that exhaust discharged from the tailpipe passes through or around the frame.

The shape and structure of the frame 12 may vary and will depend at least in part on the nature of the scent compound used. In the embodiment shown, the scent compound is of a type that may be embedded in a separate physical support or substrate 18, such as cotton. The scent-loaded substrate 18 may be replaceable or refillable. As shown, the substrate 18 may take the form of a disk with apertures to allow exhaust to pass through the frame 12. For example, the substrate 18 may be formed with a plurality of spaced apart spokes designated collectively at 20 extending radially from a hub 22 to a rim 24; this will present less obstruction to the outflow of exhaust and allow for exposure of sufficient surface area of the substrate to the flow of exhaust. Alternately, the scent compound may be formed as a part of a solid substrate and, depending on its configuration, the airflow may need to flow around the device rather than through it. That is, the frame may be a solid disk or block that releases scent in response to heat or airflow or both.

The frame 12 may comprise a cylindrical housing 28 including a front plate 30a and a back plate 30b. The front and back plates 30a and 30b may define a plurality of matching spaced-apart spokes designated collectively at 32a and 32b, respectively, extending radially from a hub 34a and 34b to a rim 36a and 36b. The rims 36a and 36b are cooperatively sized with inwardly extending flanges 38a and 38b so that one fits inside the other forming an enclosure.

Each of the spokes 32a and 32b in the front and back plates 30a and 30b defines at least one aperture. More preferably, each spoke 32a and 32b defines multiple openings designated generally at 40a and 40b, respectively. As illustrated, the spokes 20 in the substrate 18 are configured to be coextensive with the spokes 32a and 32b in the front and back plates 30a and 30b of the housing 28. In the illustrative embodiment, the inner face of the front plate 30a may define a cavity 44 configured to receive the substrate 18, as best seen in FIG. 6.

The outer diameter of the housing 28 should be about the same or slightly less than the inner diameter of the tailpipe T. In this embodiment and other applications where the scent device 10 will be in contact with hot air or exhaust, the housing 28 may be formed of or coated with or otherwise protected by a heat resistant or heat tolerant material. Although in this embodiment the housing 28 is circular in cross section, the shape may vary. For example, it may be polygonal, such as square or rectangular, or oval. While the housing 28 should have apertures to allow rapid air flow through it, the number, shape and arrangement of the apertures may vary widely. The twisted or swirled spoke design in the exemplary embodiment provides an aesthetically pleasing appearance, but the invention is not so limited. Functionally equivalent openings may be provided by a grid or mesh design.

Now it will be apparent that, when the device 10 is installed in the tailpipe T of the vehicle V (FIGS. 1-3), a portion of the vehicle exhaust passes through the openings 40a and 40b in the spokes 32a and 32b in the front and back plates 30a and 30b, as well as through the spokes 20 of the intervening substrate 18 to entrain and disperse scent. It will also be apparent that a portion of the exhaust passes unobstructed out of the tailpipe T between the spokes 32a and 32b in the front and back plates 30a and 30b and the spokes 20 of the substrate 18.

With continuing reference to FIGS. 2-4, an exemplary connector 14 will be described. In this embodiment, a clip type connector 14 is ideal as the device 10 is to be connected to the edge of the tailpipe T (FIGS. 1-3). The clip may be an alligator style clip or a suspender type clip. An ideal connector for this application may be similar to a conventional tarp clip.

Thus, the connector 14 may comprise a pair of opposing elongate jaws 48a and 48b extending from a flexible hinge 50 and is configured to grip the edge of the vehicle tailpipe T as shown. To that end, the jaws 48a and 48b may have opposing ridges or teeth. Additionally, particularly in this embodiment, the teeth as well as the jaws may be heat tolerant.

The jaws 48a and 48b are formed for movement between an open position (FIG. 4) and a closed position (FIG. 3), and the jaws are biased in the open position. A locking collar 52 is slidably movable along the length of the jaws 48a and 48b to secure the jaws in the closed position using a type of ratchet and pawl mechanism that is engaged as the collar 52 is moved toward the jaws 48a and 48b and that is released by depressing the button 54, all in a known manner.

The connector 14 may or may not be removable from the frame 12. For example, in some embodiments, the connector 14 and the frame 12 may be integrally formed. However, in the embodiment shown, the connector 14 is removably attachable to the frame 12. To that end, the device 10 may further comprise a bracket 60. A straight section 62 of the bracket is attachable to the housing 28 by some suitable means. As shown, the lower end of the straight section 62 may be attached to the center of the housing 28 using a nut 64a and bolt 64b that extends through aligned openings (not numbered) in the hubs 22, 34a, and 34b of the substrate 18 and the front and back plates 30a and 30b, respectively.

Now it will be apparent that this bolted connection serves also to secure the front and back plates 30a and 30b around the substrate 18. In this embodiment, the attachment of the connector 14 to the frame 12 is a rigid or non-movable connection. In other embodiments, the attachment may permit a hinged or pivotal movement, rotational movement, or sliding movement between the connector 14 and the frame 12.

A hook or tab 68 extends upwardly from the upper end of the straight section 62. The tab 68 is sized to be receivable between the locking collar 52 and the bottom of the clip, as depicted in FIG. 3. In the open position (FIG. 4) there a space 70 between the bottom of the hinge 50 and the collar 52 into which the tab 68 fits. As the locking collar 52 is moved toward the jaws 48a and 48b, that is, toward the closed position, the tab 68 is pinched between the collar and the hinge 50, as seen best in FIGS. 2 and 3.

Having described one embodiment of the scent device 10, its use to carry out the method of the present invention will now be explained. In accordance with the inventive method, a scent is dispersed in the vicinity of a vehicle V. The scent device 10 is connected to the exterior of the vehicle V in a location that will be exposed to airflow AF as the vehicle moves. In the embodiment shown, the vehicle is a pickup truck propelled by an internal combustion engine and comprises a tailpipe T having an open end, as seen in FIGS. 1-3. Thus, in this embodiment, the step of connecting the scent device 10 to the exterior of the vehicle V comprises connecting the scent device in or on the open end of the tailpipe T of the vehicle.

After connecting the scent device 10 to the vehicle V, air is caused to move through or around the scent device. Thus, in the exemplary embodiment, this step comprises operating the engine to drive the truck V which will cause exhaust gas to pass through the tailpipe T and the scent device 10.

Figure 7:
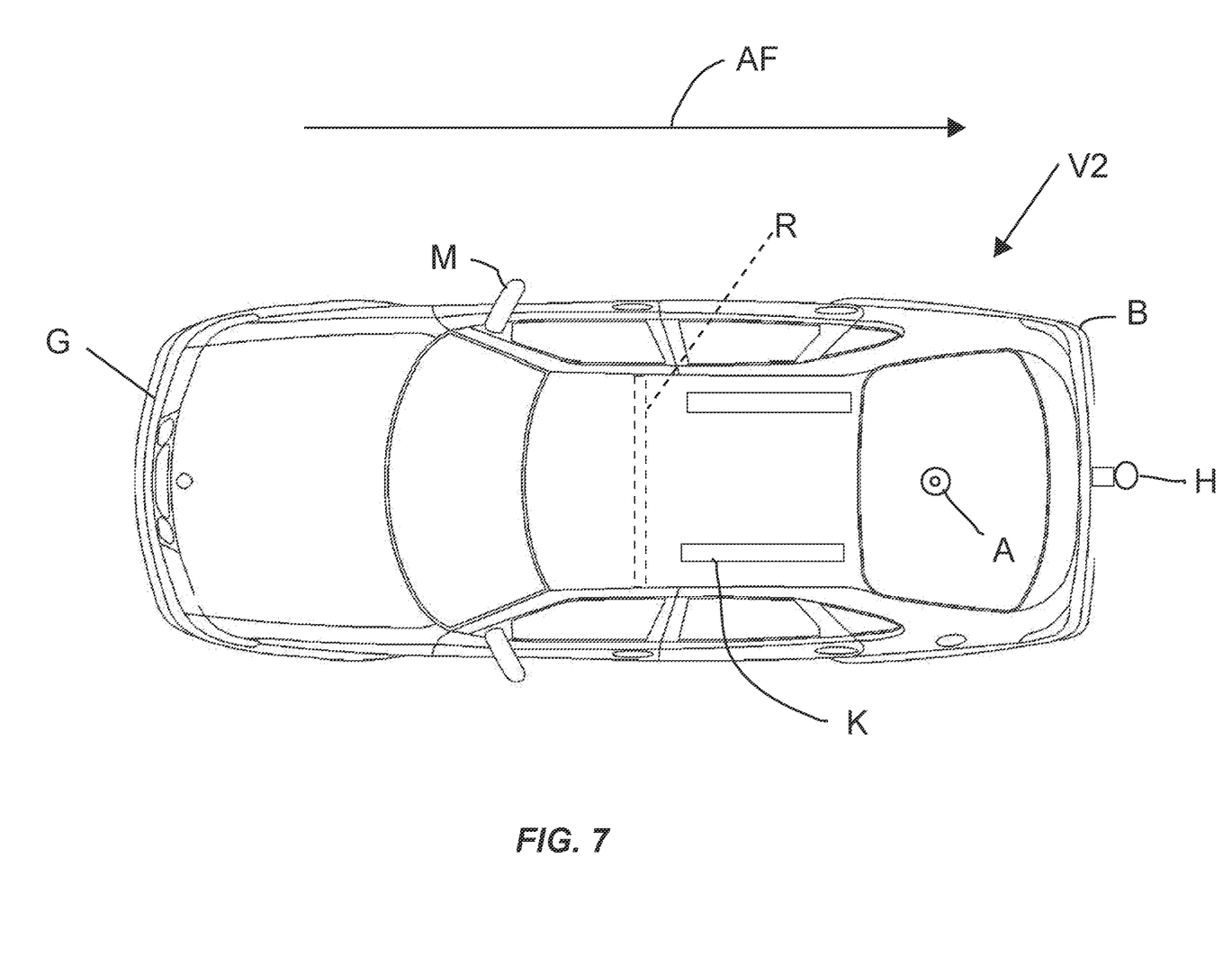
FIG. 7 is a plan view of an automobile illustrating various positions for the scent device so that air flow around the vehicle, when moving, disperses the scent.
Figure 8:
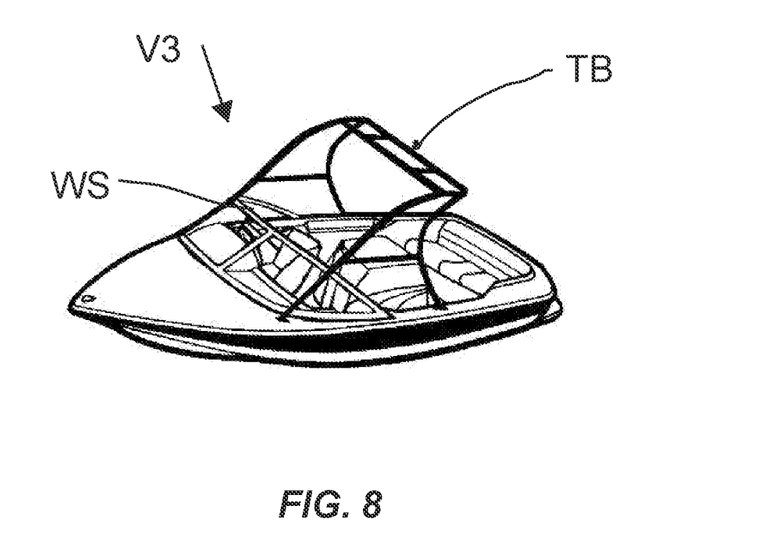
FIG. 8 is a perspective view of a boat illustrating various positions for the scent device so that airflow around the vehicle, when moving, disperses the scent.
Figure 9:
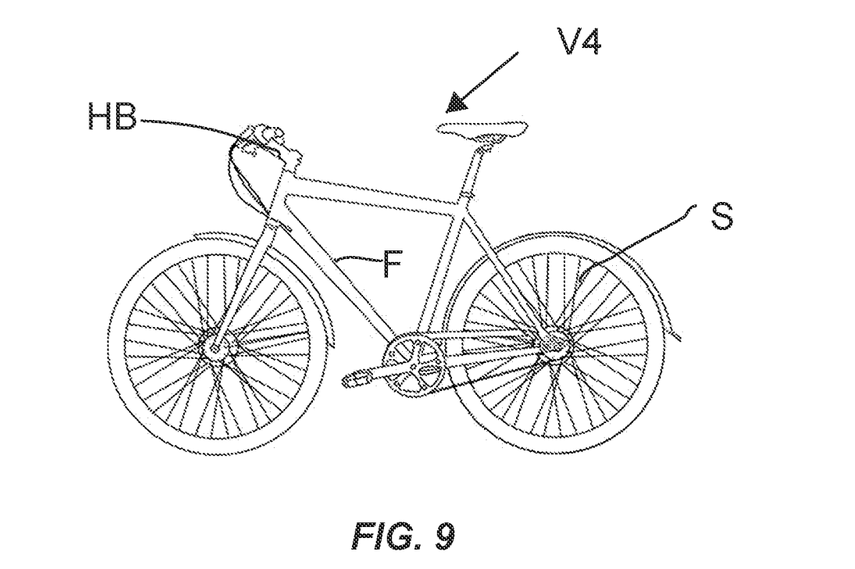
FIG. 9 is a side view of a bicycle illustrating various positions for the scent device so that airflow around the vehicle, when moving, disperses the scent.

FIG. 7 shows a plan view of a vehicle V2 which may be a sedan or SUV. The scent device 10 may be attached to the bumper B, the trailer hitch H, the side view mirror M, the antenna A, the rollover bar R, the roof rack K, or the front grille G. FIG. 8 shows a boat V3 with a tower bar TB and a windshield WS; the scent device may be connected anywhere on the tower bar or windshield. FIG. 9 shows a bicycle V4; the scent device may be connected to the handlebars HB, the spokes S, or anywhere on the frame F. Now it will be appreciated that the scent device of the present invention may be attached in many different locations on many different types of vehicles so that the moving vehicle is the mechanism for dispersing the scent into the surrounding environment.

The embodiments shown and described above are exemplary. Many details are often found in the art and, therefore, many such details are neither shown nor described herein. It is not claimed that all of the details, parts, elements, or steps described and shown herein are newly invented. Changes may be made in the details, especially in matters of shape, size, and arrangement of the parts, within the principles of the invention to the full extent indicated by the broad meaning of the terms in the attached claims. The description and drawings of the specific embodiments herein do not point out what an infringement of this patent would be, but rather provide non-limiting examples of how to use and make the invention. Likewise, the abstract is neither intended to define the invention, which is measured by the claims, nor is it intended to be limiting as to the scope of the invention in any way. The limits of the invention and the bounds of the patent protection are measured by and defined in the following claims.

What is claimed is:

1. A device for dispersing scent exterior to a vehicle, the device comprising:
    a frame for containing a dispersible scent compound, the frame configured for attachment to the exterior of the vehicle so that when the vehicle is in motion external air passes through or around the frame to disperse scent compound exterior to the vehicle;
    a connector adapted to removably connect the frame to the exterior of the vehicle; and
    a bracket having a first end removably attachable to the connector and a second end attached to the frame.

2. The device of claim 1 wherein the frame defines apertures to allow air to pass through the frame.

3. The device of claim 2 further comprising a substrate configured to fit inside the frame and to contain a dispersible scent compound for release in response to passage of air through the frame.

4. The device of claim 3 wherein the frame comprises a cylindrical housing including a front plate and a back plate, wherein the front and back plates define a plurality of matching spaced-apart spokes, wherein each of the spokes in the front and back plates defines at least one aperture, wherein the substrate comprises a physical medium formed into a disk defining a plurality of spokes, wherein the spokes in the substrate are configured to be coextensive with the spokes in the front and back plates of the frame, wherein the vehicle is motorized and comprises a tailpipe for discharging exhaust from the vehicle's motor, and whereby when the device is installed in the tailpipe of the vehicle, a portion of the vehicle exhaust passes through the spokes of the substrate to entrain and disperse scent exterior to the vehicle and a portion of the exhaust passes between the spokes of the housing unobstructed.

5. The device of claim 1 wherein the connector comprises a clip, and wherein the clip comprises:
    a flexible hinge;
    a pair of opposing elongate jaws extending from the hinge and configured to grip the edge of the vehicle tailpipe, wherein the jaws are formed for movement between an open position and a closed position, and wherein the jaws are biased in the open position;
    a locking collar slidably movable along the length of the clip to the secure the jaws in the closed position.

6. The device of claim 5 wherein the second end of the bracket terminates in a tab receivable between the locking collar and the hinge of the clip whereby, as the locking collar is moved toward the closed position, the tab on the bracket is pinched between the collar and the hinge.

7. The device of claim 1 wherein the frame, the bracket and the connector are heat tolerant.

8. An assembly comprising a vehicle and the device of claim 1 connected to the vehicle.

* * * * *